United States Patent
Yoshimitsu et al.

(10) Patent No.: US 11,337,898 B2
(45) Date of Patent: May 24, 2022

(54) DENTAL FLUOROALUMINOSILICATE GLASS POWDER

(71) Applicant: GC Corporation, Shizuoka (JP)

(72) Inventors: Ryosuke Yoshimitsu, Tokyo (JP); Yusuke Shimada, Tokyo (JP); Ayaka Fujimoto, Tokyo (JP); Naofumi Matsumoto, Tokyo (JP); Mizuki Nakayama, Tokyo (JP)

(73) Assignee: GC Corporation, Shizuoka (JP)

( * ) Notice: Subject to any disclaimer, the term of this patent is extended or adjusted under 35 U.S.C. 154(b) by 0 days.

(21) Appl. No.: 17/056,827

(22) PCT Filed: May 8, 2019

(86) PCT No.: PCT/JP2019/018351
§ 371 (c)(1),
(2) Date: Nov. 19, 2020

(87) PCT Pub. No.: WO2019/230309
PCT Pub. Date: Dec. 5, 2019

(65) Prior Publication Data
US 2021/0196580 A1     Jul. 1, 2021

(30) Foreign Application Priority Data
May 30, 2018   (JP) .............. JP2018-103396

(51) Int. Cl.
*A61K 6/889* (2020.01)
*A61K 6/836* (2020.01)
*A61K 6/17* (2020.01)

(52) U.S. Cl.
CPC ............ *A61K 6/889* (2020.01); *A61K 6/17* (2020.01); *A61K 6/836* (2020.01)

(58) Field of Classification Search
CPC ....................................... A61K 6/889
See application file for complete search history.

(56) References Cited

U.S. PATENT DOCUMENTS 9,937,107 B2    4/2018  Hokii et al.
2016/0310368 A1* 10/2016  Peez .............. A61K 6/889

FOREIGN PATENT DOCUMENTS

| EP | 3552596 | 10/2019 |
| JP | H05-331017 | 12/1993 |
| WO | 2015/088956 | 6/2015 |
| WO | 2016/002600 | 1/2016 |
| WO | 2017/015193 | 1/2017 |
| WO | 2017/083039 | 5/2017 |

OTHER PUBLICATIONS

International Search Report for PCT/JP2019/018351 dated Jun. 25, 2019.

* cited by examiner

*Primary Examiner* — Michael F Pepitone
(74) *Attorney, Agent, or Firm* — IPUSA, PLLC

(57) ABSTRACT

One aspect of the present invention relates to a dental fluoroaluminosilicate glass powder, a 50th percentile volume diameter of which is 5.0 μm or more and 9.0 μm or less, and a 10th percentile volume diameter of which is 2.4 μm or more.

8 Claims, No Drawings

DENTAL FLUOROALUMINOSILICATE GLASS POWDER

The present application is a national-phase application of the international application No. PCT/JP2019/018351 filed on May 8, 2019, claiming priority to the Japanese patent application No. 2018-103396 filed on May 30, 2018, the entire contents of which are incorporated herein by reference.

FIELD OF THE INVENTION

The present invention relates to a dental fluoroaluminosilicate glass powder and a glass ionomer cement.

BACKGROUND OF THE INVENTION

A glass ionomer cement has excellent characteristics, for example, extremely favorable biocompatibility, excellent aesthetic property of semi-transparent cured product, excellent adhesion to tooth substrates such as enamel and dentine, and anticariogenic effect by the fluoride. Thus, the glass ionomer cement is widely used in dentistry, for example for filling cavities of dental caries, for luting crowns, inlays, bridges and orthotic bands, for cavity linings, sealers for filling root canals, core build up, fissure sealant, and the like.

A glass ionomer cement generally has an aqueous solution of polycarboxylic acid-based polymer and fluoroaluminosilicate glass powder (for example, refer to Patent Document 1).

Here, when an aqueous solution of polycarboxylic acid-based polymer and a fluoroaluminosilicate glass powder are mixed, an aluminum ion ($Al^{3+}$) released from the fluoroaluminosilicate glass powder and the conjugate base of the polycarboxylic acid-based polymer are conically cross-linked and cured by the acid-base reaction of the fluoroaluminosilicate glass powder and the polycarboxylic acid-based polymer.

RELATED-ART DOCUMENT

Patent Documents

Patent Document 1: International Publication No. WO2016/002600

SUMMARY OF THE INVENTION

Problems to be Solved by the Invention

Generally, the compressive strength of the cured product of glass ionomer cement is desired to be improved. For this purpose, a fluoroaluminosilicate glass powder having a small particle size is considered to be used.

However, when a fluoroaluminosilicate glass powder having a small particle size is used, the problem arises that the time from the start of mixing a fluoroaluminosilicate glass powder with an aqueous solution of polycarboxylic acid-based polymer to the curing thereof, that is, the working time of the glass ionomer cement, becomes shorter.

An aspect of the present invention has the object of providing a dental fluoroaluminosilicate glass powder capable of extending the working time of the glass ionomer cement and of increasing the compressive strength of the cured product of the glass ionomer cement.

Means for Solving the Problems

One aspect of the present invention relates to a dental fluoroaluminosilicate glass powder, a 50th percentile volume diameter of which is 5.0 µm or more and 9.0 µm or less, and a 10th percentile volume diameter of which is 2.4 µm or more.

Effects of the Invention

In one aspect of the present invention, a dental fluoroaluminosilicate glass powder can be provided that is capable of extending the working time of the glass ionomer cement and of increasing the compressive strength of the cured product of the glass ionomer cement.

DETAILED DESCRIPTION

In the following, embodiments for carrying out the present invention will be described.

<Dental Fluoroaluminosilicate Glass Powder>

The 50th percentile volume diameter (d50) of the dental fluoroaluminosilicate glass powder of the present embodiment is 5.0 µm or more and 9.0 µm or less, and is preferably 5.1 µm or more and 8.0 µm or less. When the d50 of the dental fluoroaluminosilicate glass powder is less than 5.0 µm, the working time of the glass ionomer cement becomes shorter. On the other hand, when the d50 of the dental fluoroaluminosilicate glass powder exceeds 9.0 µm, the compressive strength of the cured product of the glass ionomer cement is decreased.

The 10th percentile volume diameter (d10) of the dental fluoroaluminosilicate glass powder of the present embodiment is 2.4 µm or more, and is preferably 2.7 µm or more. When the d10 of the dental fluoroaluminosilicate glass powder is less than 2.4 µm, the aqueous solution of the polycarboxylic acid-based polymer and the dental fluoroaluminosilicate glass powder cannot be mixed.

The d10 of the dental fluoroaluminosilicate glass powder of the present embodiment is usually 4.8 µm or less.

The 90th percentile volume diameter (d90) of the dental fluoroaluminosilicate glass powder of the present embodiment is 13.0 µm or more and 20.0 µm or less, and is preferably 14.0 µm or more and 19.0 µm or less. When the d90 of the dental fluoroaluminosilicate glass powder of the present embodiment is 13.0 µm or more, the working time of the glass ionomer cement is extended. When the d90 of the dental fluoroaluminosilicate glass powder of the present embodiment is 20 µm or less, the compressive strength of the cured product of the glass ionomer cement is increased.

The content of fluorine (F) in the dental fluoroaluminosilicate glass powder of the present embodiment is preferably 1 to 30% by mass and more preferably 3 to 20% by mass.

The content of aluminum in the dental fluoroaluminosilicate glass powder of the present embodiment is preferably 15 to 35% by mass and more preferably 20 to 30% by mass in terms of the amount converted to aluminum oxide ($Al_2O_3$).

The content of silicon in the dental fluoroaluminosilicate glass powder of the present embodiment is preferably 15 to 50% by mass and more preferably 20 to 40% by mass in terms of the amount converted to silicon oxide ($SiO_2$).

The content of phosphorus in the dental fluoroaluminosilicate glass powder of the present embodiment is preferably 0 to 10% by mass and more preferably 1 to 5% by mass in terms of the amount converted to phosphorus (V) oxide ($P_2O_5$).

The content of sodium in the dental fluoroaluminosilicate glass powder of the present embodiment is preferably 0 to 15% by mass and more preferably 1 to 10% by mass in terms of the amount converted to sodium oxide ($Na_2O$).

The content of potassium in the dental fluoroaluminosilicate glass powder of the present embodiment is preferably 0 to 10% by mass and more preferably 1 to 5% by mass in terms of the amount converted to potassium oxide ($K_2O$).

The content of strontium in the dental fluoroaluminosilicate glass powder of the present embodiment is preferably 0 to 40% by mass and more preferably 10 to 30% by mass in terms of the amount converted to strontium oxide (SrO).

The content of lanthanum in the dental fluoroaluminosilicate glass powder of the present embodiment is preferably 0 to 50% by mass and more preferably 1 to 40% by mass in terms of the amount converted to lanthanum oxide ($La_2O_3$).

The dental fluoroaluminosilicate glass powder of the present embodiment can be applied to, for example, a glass ionomer cement or the like.

<Glass Ionomer Cement>

The glass ionomer cement of the present embodiment contains the dental fluoroaluminosilicate glass powder of the present embodiment and an aqueous solution of a polycarboxylic acid-based polymer.

The polycarboxylic acid-based polymer is not particularly limited, but for example, a homopolymer or copolymer of α,β-unsaturated carboxylic acid can be used.

Examples of the α,β-unsaturated carboxylic acid include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, and the like.

In addition, the polycarboxylic acid-based polymer may be a copolymer of an α,β-unsaturated carboxylic acid and a monomer capable of copolymerizing with the α,β-unsaturated carboxylic acid.

Examples of the component that can be copolymerized with the α,β-unsaturated carboxylic acid include acrylamide, acrylonitrile, methacrylic acid ester, acrylates, vinyl chloride, allyl chloride, vinyl acetate, and the like.

In this case, the ratio of the α,β-unsaturated carboxylic acid to the monomer constituting the polycarboxylic acid-based polymer is preferably 50% by mass or more.

The polycarboxylic acid-based polymer is preferably a homopolymer or copolymer of acrylic acid or itaconic acid.

Note that at least a part of the polycarboxylic acid-based polymer may be powder.

In the glass ionomer cement of the present embodiment, when the dental fluoroaluminosilicate glass powder and the aqueous solution of the polycarboxylic acid-based polymer are mixed, the mass ratio of the dental fluoroaluminosilicate glass powder with respect to the aqueous solution of the polycarboxylic acid-based polymer (hereinafter referred to as powder-liquid ratio) is preferably 1 to 5 and more preferably 2.8 to 4.0. When the powder-liquid ratio is 1 or more, the compressive strength of the cured product of the glass ionomer cement is further increased. When the powder-liquid ratio is 5 or less, the dental fluoroaluminosilicate glass powder and the aqueous solution of the polycarboxylic acid-based polymer are easily mixed.

EXAMPLES

Examples of the present invention will be described below, but the present invention is not limited to the examples.

<Preparation of Fluoroaluminosilicate Glass Powder>

28 g of silica ($SiO_2$), 10 g of alumina ($Al_2O_3$), 18 g of aluminum fluoride ($AlF_3$), 17 g of strontium fluoride ($SrF_2$), 11 g of aluminum phosphate ($AlPO_4$), 6 g of cryolite ($Na_3AlF_6$), 6 g of potassium fluoride (KF) and 3 g of lanthanum oxide ($La_2O_3$) were sufficiently mixed using a mortar. The obtained mixture was put into a magnetic crucible and left standing in an electric furnace. The temperature of the electric furnace was raised to 1300° C., the mixture was melted and homogenized sufficiently, and then poured into water to obtain a bulk fluoroaluminosilicate glass. The obtained bulk fluoroaluminosilicate glass was crushed with a ball mill for 20 hours and then passed through a 120-mesh sieve to obtain fluoroaluminosilicate glass powder.

It was confirmed that the obtained fluoroaluminosilicate glass powder contained the following composition by the fluorescent X-ray analysis.

F: 18% by mass
$Na_2O$: 3% by mass
$Al_2O_3$: 22% by mass
$SiO_2$: 22% by mass
$P_2O_5$: 5% by mass
$K_2O$: 5% by mass
SrO: 21% by mass
$La_2O_3$: 4% by mass The obtained fluoroaluminosilicate glass powder was further pulverized using a ball mill to adjust the particle size distribution, to obtain fluoroaluminosilicate glass powders of Examples 1 to 6 and Comparative Examples 1 to 3.

<Particle Size Distribution of Fluoroaluminosilicate Glass Powder>

The particle size distribution of the fluoroaluminosilicate glass powder was measured using a laser diffraction/scattering particle size distribution measuring device LA-950 (manufactured by HORIBA Ltd.). Specifically, first, fluoroaluminosilicate glass powder was dispersed in a 0.1% by mass of hexametaphosphoric acid aqueous solution to obtain a suspension. Next, a small amount (0.5 ml) of the suspension was added to circulated 0.1% by mass of hexametaphosphoric acid aqueous solution, and the particle size distribution of the fluoroaluminosilicate glass powder was measured.

<Working time of Glass Ionomer Cement>

The fluoroaluminosilicate glass powder and a 50% by mass of polyacrylic acid aqueous solution were mixed at a predetermined powder-liquid ratio (see Table 1). Next, the mixed product was pulled up with a spatula, with the spatula being in contact with the mixed product of glass ionomer cement, and the operation of confirming whether the mixed product of glass ionomer cement adheres to the spatula was repeated. Thereby, the time at which the mixed product of the glass ionomer cement no longer adhered to the spatula after the start of mixing of the fluoroaluminosilicate glass powder and the 50% by mass of polyacrylic acid-based aqueous solution was measured. The time measured was considered as the working time of the glass ionomer cement.

The criteria for determining the working time of the glass ionomer cement was as follows.

Excellent: the working time of the glass ionomer cement was 1 minute 30 seconds or more.

Good: the working time of the glass ionomer cement was 1 minute 15 seconds or more and less than 1 minute 30 seconds.

Not good: the working time of the glass ionomer cement was less than 1 minute 15 seconds.

<Compressive Strength of Cured Product of Glass Ionomer Cement>

The fluoroaluminosilicate glass powder and a 50% by mass of polyacrylic acid aqueous solution were mixed at a predetermined powder-liquid ratio (see Table 1) to obtain a mixed product of glass ionomer cement. Next, 4.2 g of a mixed product of glass ionomer cement was filled in a mold having a height of 6 mm and a diameter of 4 mm, and was pressure-contacted and then allowed to stand in a thermostatic chamber at 37° C. and 100% RH for 1 hour. After the mold was taken out from the thermostatic chamber, the cured product of the glass ionomer cement was removed from the mold and immersed in water at 37° C. for 24 hours. Next, the water of the cured product of the glass ionomer cement was wiped off. Then, a load was applied in the longitudinal direction of the cured product of the glass ionomer cement using the precision universal testing machine (autograph) (manufactured by Shimadzu Corp.), and the load when the cured product of the glass ionomer cement was broken was measured (hereinafter, referred to as the maximum load).

Next, the compressive strength C [MPa] of the cured product of the glass ionomer cement was calculated by the formula:

$$C = 4p/(\pi d^2)$$

Here, p is the maximum load [N], and d is the diameter [mm] of the cured product of the glass ionomer cement.

The criteria for determining the compressive strength of the cured product of the glass ionomer cement was as follows.

Good: the compressive strength of the cured product of the glass ionomer cement was 200 MPa or more.

Not good: the compressive strength of the cured product of the glass ionomer cement was less than 200 MPa.

Table 1 shows the working time of the glass ionomer cement and the evaluation results of the compressive strength of the cured product of the glass ionomer cement.

TABLE 1

|  | Examples | | | | | | Comparative Examples | | |
|---|---|---|---|---|---|---|---|---|---|
|  | 1 | 2 | 3 | 4 | 5 | 6 | 1 | 2 | 3 |
| d10 [μm] | 3.0 | 2.7 | 3.2 | 2.8 | 2.4 | 3.2 | 4.7 | 2.0 | 1.3 |
| d50 [μm] | 6.3 | 5.1 | 6.9 | 5.8 | 6.3 | 6.9 | 10.1 | 5.0 | 2.1 |
| d90 [μm] | 16.2 | 14.0 | 18.1 | 16.8 | 13.2 | 18.1 | 18.5 | 9.1 | 3.6 |
| Powder-liquid ratio | 3.2 | 3.2 | 3.2 | 3.2 | 3.2 | 3.4 | 3.2 | 3.2 | 3.2 |
| Working time | 1'30" | 1'30" | 1'40" | 1'40" | 1'15" | 1'15" | 1'50" | — | — |
|  | Excellent | Excellent | Excellent | Excellent | Good | Good | Excellent | — | — |
| Compressive strength [MPa] | 262 | 241 | 220 | 235 | 210 | 249 | 182 | — | — |
|  | Good | Good | Good | Good | Good | Good | Not good | — | — |

From Table 1, when the fluoroaluminosilicate glass powders of Examples 1 to 6 were used, the working time of the glass ionomer cement was extended, and the compression strength of the hardened glass ionomer cement was increased.

On the other hand, the d50 of the fluoroaluminosilicate glass powder in Comparative Example 1 was 10.1 μm. As a result, the compressive strength of the cured product of the glass ionomer cement was decreased.

Further, the d10 of the fluoroaluminosilicate glass powder in Comparative Examples 2 and 3 were 2.0 μm and 1.3 μm, respectively. As a result, the fluoroaluminosilicate glass powder in Comparative Examples 2 and 3 were not able to be mixed with 50% by mass of polyacrylic acid aqueous solution.

This international application is based on and claims priority of Japanese Patent Application No. 2018-103396 filed May 30, 2018, the entire contents of which are hereby incorporated by reference.

The invention claimed is:
1. A dental fluoroaluminosilicate glass powder, the glass powder comprising particles having
  a 50th percentile volume diameter of 5.0 μm or more and 9.0 μm or less,
  a 10th percentile volume diameter of 2.4 μm or more, and
  a 90th percentile volume diameter of 16.2 μm or more and 20.0 μm or less.
2. The dental fluoroaluminosilicate glass powder according to claim 1, wherein the powder is for a glass ionomer cement.
3. A glass ionomer cement comprising:
  the dental fluoroaluminosilicate glass powder of claim 1; and
  an aqueous solution of a polycarboxylic acid-based polymer.
4. The dental fluoroaluminosilicate glass powder according to claim 1, wherein the powder comprises:
  1 to 30% by mass of fluorine;
  0 to 15% by mass of sodium oxide;
  15 to 35% by mass of aluminum oxide;
  15 to 50% by mass of silicon oxide,
  0 to 10% by mass of phosphorus(V) oxide;
  0 to 10% by mass of potassium oxide;
  0 to 40% by mass of strontium oxide; and
  0 to 50% by mass of lanthanum oxide.
5. The dental fluoroaluminosilicate glass powder according to claim 1, wherein a mass ratio of the dental fluoroaluminosilicate glass powder with respect to an aqueous solution of a polycarboxylic acid-based polymer is 2.8 to 4.0.
6. The dental fluoroaluminosilicate glass powder according to claim 1, wherein the 10th percentile volume diameter of 3.2 μm or more and 4.8 μm or less.
7. The glass ionomer cement according to claim 3, wherein a working time of the glass ionomer cement is 1 minute 15 seconds or more.
8. The glass ionomer cement according to claim 3, wherein a compressive strength of a cured product of the glass ionomer cement is 200 MPa or more.

* * * * *